United States Patent
Ko et al.

(10) Patent No.: US 9,226,725 B2
(45) Date of Patent: Jan. 5, 2016

(54) PHYSIOLOGICAL SIGNALS SENSING STRUCTURE, STETHOSCOPE THEREWITH AND MANUFACTURING METHOD THEREOF

(71) Applicants: Wen-Ching Ko, Kaohsiung (TW); Kuo-Hua Tseng, New Taipei (TW); Chang-Ho Liou, Changhua County (TW); Chang-Yi Chen, Hsinchu (TW)

(72) Inventors: Wen-Ching Ko, Kaohsiung (TW); Kuo-Hua Tseng, New Taipei (TW); Chang-Ho Liou, Changhua County (TW); Chang-Yi Chen, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 563 days.

(21) Appl. No.: 13/628,056

(22) Filed: Sep. 27, 2012

(65) Prior Publication Data

US 2013/0310709 A1 Nov. 21, 2013

(30) Foreign Application Priority Data

May 17, 2012 (TW) .............................. 101117610 A

(51) Int. Cl.
*A61B 7/04* (2006.01)
*H04R 25/00* (2006.01)
(Continued)

(52) U.S. Cl.
CPC .. *A61B 7/02* (2013.01); *H04R 1/46* (2013.01); *G01H 11/08* (2013.01)

(58) Field of Classification Search
CPC ............ A61B 7/02; G01H 11/08; H04R 1/46; H04R 17/00; H04R 17/005; H04R 2217/00; H04R 2217/01; H04R 2217/03

USPC ............ 381/67, 173, 190, 430; 156/286, 292; 600/586

See application file for complete search history.

(56) References Cited

U.S. PATENT DOCUMENTS

| 4,985,195 A | * | 1/1991 | Wilson et al. ................. 264/320 |
| 5,557,681 A | | 9/1996 | Thomasson |

(Continued)

FOREIGN PATENT DOCUMENTS

| CN | 1338909 | 3/2002 |
| CN | 1646887 | 7/2005 |

(Continued)

OTHER PUBLICATIONS

"Office Action of Taiwan Counterpart Application", issued on Dec. 12, 2014, p. 1-p. 6, in which the listed references were cited.

(Continued)

*Primary Examiner* — Khai N Nguyen
(74) *Attorney, Agent, or Firm* — Jianq Chyun IP Office

(57) ABSTRACT

A physiological signal sensing structure, a stethoscope therewith, and a manufacturing method thereof are provided. The sensing structure for physiological signals includes a flexible substrate, a piezoelectric sensing structure and a damping structure. The piezoelectric sensing structure is disposed over the flexible substrate, and includes a first surface and a second surface. The second surface of the piezoelectric sensing structure faces the flexible substrate. The piezoelectric sensing structure is an arc with a curvature, and the first surface thereof may face outward. The damping structure may be disposed between the flexible substrate and the piezoelectric sensing structure. In an embodiment, a further amplifying structure is disposed over the first surface of the piezoelectric sensing structure and contacts or does not contact a top region of the first surface.

21 Claims, 7 Drawing Sheets

(51) Int. Cl.
*A61B 7/02* (2006.01)
*H04R 1/46* (2006.01)
*G01H 11/08* (2006.01)

(56) References Cited

U.S. PATENT DOCUMENTS

| | | | |
|---|---|---|---|
| 6,533,736 | B1 | 3/2003 | Moore |
| 6,661,161 | B1 | 12/2003 | Lanzo et al. |
| 7,806,833 | B2 | 10/2010 | Thiagarajan et al. |
| 7,991,165 | B2 | 8/2011 | Kassal et al. |
| 2003/0043216 | A1* | 3/2003 | Usui et al. ............ 347/7 |
| 2004/0039294 | A1 | 2/2004 | Sullivan et al. |
| 2004/0112139 | A1* | 6/2004 | Ogino et al. ............ 73/756 |
| 2005/0049514 | A1 | 3/2005 | Iwamiya et al. |
| 2005/0232434 | A1* | 10/2005 | Andersen ............ 381/67 |
| 2007/0080610 | A1* | 4/2007 | Sato et al. ............ 310/348 |
| 2007/0113649 | A1* | 5/2007 | Bharti et al. ............ 73/431 |
| 2008/0093157 | A1* | 4/2008 | Drummond et al. ....... 181/131 |
| 2008/0137876 | A1* | 6/2008 | Kassal et al. ............ 381/67 |
| 2009/0069689 | A1* | 3/2009 | Isono ............ 600/459 |
| 2009/0211838 | A1 | 8/2009 | Bilan |
| 2011/0166459 | A1 | 7/2011 | Kopetsch et al. |
| 2011/0319021 | A1* | 12/2011 | Proulx et al. ............ 455/41.2 |
| 2012/0190303 | A1* | 7/2012 | Wong ............ 455/41.2 |
| 2012/0226201 | A1* | 9/2012 | Clark et al. ............ 601/3 |
| 2013/0134834 | A1* | 5/2013 | Yoshikawa et al. ........ 310/341 |

FOREIGN PATENT DOCUMENTS

| | | |
|---|---|---|
| CN | 1679372 | 10/2005 |
| CN | 200963147 | 10/2007 |
| JP | 2008-142356 | 6/2008 |
| KR | 100838251 | 6/2008 |
| TW | M247177 | 10/2004 |
| TW | I245621 | 12/2005 |
| TW | I319313 | 1/2010 |
| TW | I322043 | 3/2010 |
| WO | 2008143463 | 11/2008 |

OTHER PUBLICATIONS

"Office Action of China Counterpart Application", issued on Sep. 9, 2014, p. 1-p. 6, in which the listed references were cited.

Zhang et al., "Design of a Flexible Stethoscope Sensor Skin Based on MEMS Technology", 7th International Conference on Electronics Packaging Technology, 2006, p. 1-p. 4.

Udawatta et al., "Knowledge on Heart Patients Through Stethoscopic Cardiac Murmur Identification for E-Healthcare", 8th International Conference on ICT, 2010, p. 1-p. 6.

* cited by examiner

PHYSIOLOGICAL SIGNALS SENSING STRUCTURE, STETHOSCOPE THEREWITH AND MANUFACTURING METHOD THEREOF

CROSS-REFERENCE TO RELATED APPLICATION

This application claims the priority benefit of Taiwan application serial no. 101117610, filed on May 17, 2012. The entirety of the above-mentioned patent application is hereby incorporated by reference herein and made a part of this specification.

TECHNICAL FIELD

The disclosure relates to a physiological signals sensing structure, stethoscope therewith and manufacturing method thereof.

BACKGROUND

In recent years, as material life improves, people have become more conscious concerning the issues of health. Most people are unaware of their current health condition or environmental condition, and overlook signals emitted by their body. Thus, in order to let the public be able to observe their own physiological condition, various measuring devices having been gradually emerging. As such, the public can use the various measuring devices to monitor their own physiological condition, and immediately determine if there are any unusual problems occurred with their health condition. By this manner, the user can pay more attention to their physical condition, and make any suitable adjustments.

Currently, regarding monitoring physiological signals for health conditions, heart sounds and lung sounds are some valuable factors for consideration. During a heart cycle, since the heart muscles contract and expand, the valves inside the heart open and close, and blood flow beats against the heart chamber wall and the aorta wall, some turbulences are formed, which causes some vibration that transmits to the surface of chest. When a stethoscope is placed at a specific position of the surface of chest, some heart sounds are heard, which may be used to determine if the heart is normal or not.

Lung sounds are also acoustic signals, which occur mainly from gas exchanging in the alveolus of the lung lobe. The oxygen in air can be absorbed by the body, and the carbon dioxide in the body can be disposed of at the same time. The lungs undergo contraction and expansion, which drives the gas flow, and then the sound is generated through the air flow vibration in the breathing passage. Through confirmation from related research, the strength of the lung sound is related to the air flow rate in the breathing passage, and the frequency distribution of the lung sound is related to the tension of the breathing passage. The frequency distribution of lung sound is very broad, ranging from 100 Hz to around 2000 Hz, and the frequency spectrum is different according to different measuring positions.

In the current technical fields, sensing heart sounds at a specific frequency range from 10 Hz to 1 kHz has a specific purpose. For example, signals sensed in a low frequency range (15-400 Hz) can be used to determine if the heart is normal or not. Through the auscultation using a stethoscope by a physician or through a microphone or a micro-electro-mechanical system (MEMS), these signals can be sensed to obtain a phonocardiogram (PCG) for the physician to observe.

SUMMARY

The disclosure provides a physiological signal sensing structure, including a flexible substrate, a piezoelectric sensing structure, and a damping structure. The piezoelectric sensing structure is disposed over the flexible substrate, and includes a first surface and a second surface. The second surface of the piezoelectric sensing structure faces the flexible substrate. The piezoelectric sensing structure is an arc with a certain curvature, and the first surface thereof faces outward. The damping structure is disposed between the flexible substrate and the piezoelectric sensing structure.

The disclosure provides a stethoscope, including a plurality of physiological signal sensing structures. Each physiological signal sensing structure includes a flexible substrate, a piezoelectric sensing structure, and a damping structure. The piezoelectric sensing structure is disposed over the flexible substrate, and includes a first surface and a second surface. The second surface of the piezoelectric sensing structure faces the flexible substrate. The piezoelectric sensing structure is an arc with a certain curvature, and the first surface thereof faces outward. The damping structure is disposed between the flexible substrate and the piezoelectric sensing structure.

In an embodiment, the physiological signal sensing structure or the stethoscope further includes an amplifying structure, disposed over a curved surface area of the first surface of the piezoelectric sensing structure, and contacts or does not contact a top region of the arc of the curved surface area The disclosure further provides a manufacturing method of a physiological signal sensing structure. The method includes providing a piezoelectric sensor sheet and mold, wherein the mold includes a wave surface; softening the piezoelectric sensor sheet so as to tightly adhere to the wave surface; solidifying the piezoelectric sensor sheet; and fixing the piezoelectric sensor sheet to a flexible substrate.

In an embodiment of the method of manufacturing the physiological signal sensor structure, after solidifying the piezoelectric sensor sheet, damping material is disposed on the flexible substrate. The piezoelectric sensor sheet is fixed on the flexible substrate, and a damping structure is formed between the flexible substrate and a curved surface area of the piezoelectric sensor sheet.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
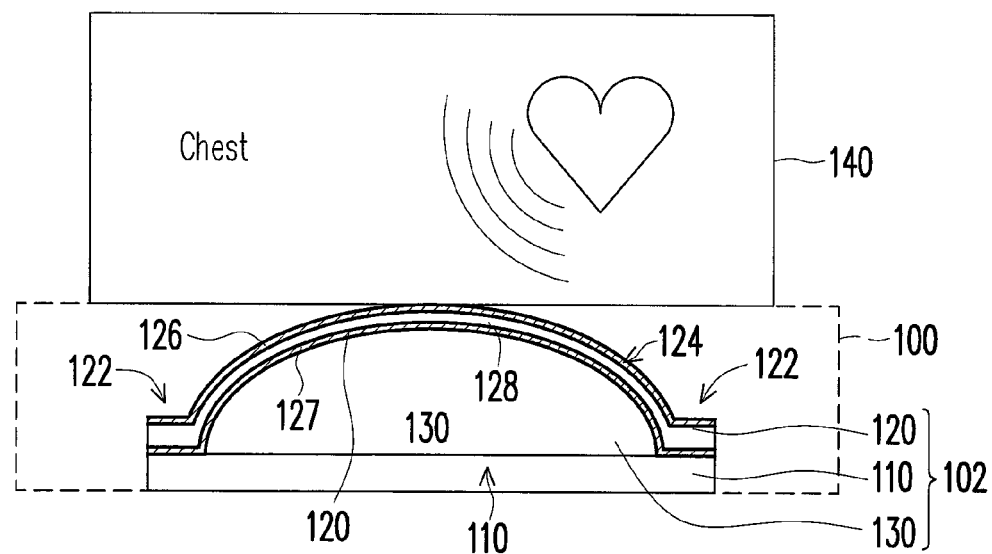
FIG. 1 is a schematic view of a physiological signal sensor structure according to an embodiment of the disclosure.

The disclosure provides a physiological signal sensing structure, which may be thin and/or flexible. A portion of the structure may contact skin. Since the portion contacting the skin is a soft material close to the acoustic impedance coefficient of muscles, such as plastic material, thus, the body's physiological signal, such as heart sound or lung sound, may be effectively obtained by the physiological signal sensing structure.

In an embodiment of the disclosure, a physiological signal sensing structure may include a piezoelectric sensing structure with a curvature, a flexible substrate, and a damping structure disposed between the piezoelectric sensing structure and the flexible substrate. The piezoelectric sensing structure is disposed over the flexible substrate. The piezoelectric sensing structure includes a curved surface area and an edge area. The piezoelectric sensing structure includes a first surface and a second surface. The second surface faces the flexible substrate. The curved surface area of the piezoelectric sensing structure is an arc with a certain curvature, faces outward as the first surface.

In the embodiment, the piezoelectric sensing structure with the curved surface area with a certain curvature may have a part of the first surface contact the surface of the skin of the person to be sensed. When the sound of the physiological signals of the body, such as heart sound or lung sound, reaches the surface of the skin, the amplitude of the sound drives the piezoelectric sensing structure to vibrate. The physiological signal sensing structure amplifies the amplitude of the sounds, so as to sense and obtain the physiological signal of the body.

A damping structure may be disposed between the piezoelectric sensing structure and the flexible substrate. The damping structure may include a material such as air, foam, or soft plastic. Other material with the similar damping function may be used and is within the scope and spirit of the disclosure.

In another embodiment of the disclosure, a physiological signal sensing structure may include a piezoelectric sensing structure with a curvature, a flexible substrate, and a damping structure disposed between the piezoelectric sensing structure and the flexible substrate. In addition, the physiological signal sensing structure further includes an amplifying structure, disposed on a surface of the piezoelectric sensing structure not facing the flexible substrate, and contacts the piezoelectric sensing structure. The amplifying structure may planarly and tightly contact the skin of the person to be sensed. In an embodiment, the amplifying structure, for example, may include a protruding structure contacting the piezoelectric sensing structure. When the sound of the physiological signals of the body, for example heart sound or lung sound, reaches the surface of the skin, the amplitude of the sound drives the amplifying structure. The amplifying structure uses, for example, the protruding structure to transmit the sound to the piezoelectric sensing structure, so as to amplify the amplitude of the sound that is transmitted. The physiological signals of the body may be conveniently sensed and obtained therefrom.

In some of embodiments of the disclosure, a physiological signal sensing structure may, for example, amplify heart sound through a mechanical amplifying structure. By the mechanical amplifying structure, low frequency signals may be effectively amplified and transmitted to the piezoelectric sensing structure. The piezoelectric sensing structure with a certain curvature is, for example, a piezoelectric sensing structure with an arc structure, and may effectively sense low frequency vibration.

The disclosure provides a flexible stethoscope, including an arrangement of a plurality of physiological signal sensing structures with a pattern. The distribution of the pattern may be arranged as an array, or the distribution of the pattern may be arranged arbitrarily on a same surface. The arrangement of the plurality of physiological signal sensing structures with a pattern may broaden the sensing area for the physiological signals.

In a physiological signal sensing structure or a stethoscope therewith provided by the disclosure may be used to detect heart sound or lung sound, increase a signal to noise ratio with a simple structure using a simple circuit. The embodiments of the disclosure may have low production cost, high sensitivity, good low frequency response, and partial or complete flexibility.

The disclosure further provides a method of manufacturing the physiological signal sensing structure. In an embodiment, the manufacturing method includes providing a piezoelectric sensor sheet and a mold. The mold includes a wave surface. After the piezoelectric sensor sheet is heated and softened, it is tightly adhered to the non-continuous wave surface of the mold. Next, the piezoelectric sensor sheet is cooled and solidified, so as to form a piezoelectric sensing structure with one or more curvatures. Then the piezoelectric sensing structure with an arc structure is fixed to the flexible substrate.

The disclosure further provides a method of manufacturing the physiological signal sensing structure, including providing a piezoelectric sensor sheet and a mold. The mold includes a wave surface. After the piezoelectric sensor sheet is heated and softened, it may adhere to the non-continuous wave surface of the mold. The piezoelectric sensor sheet is cooled and solidified, to form a piezoelectric sensing structure with one or more curvatures. After the piezoelectric sensor sheet is solidified, the damping material may dispose over the flexible substrate. The piezoelectric sensor sheet adheres to the flexible substrate, and a damping structure may form between the flexible substrate and the curved surface area of the piezoelectric sensor sheet.

In order to more clearly understand the disclosure, the following presents an exemplary embodiment for further description.

FIG. 1 is a schematic view of a physiological signal sensing structure according to an embodiment of the disclosure.

Referring to FIG. 1, in the embodiment, a stethoscope 100 includes a plurality of physiological signal sensing structures 102, arranged on a surface or a flat panel, such as the same flexible substrate 110. In an embodiment, an array-type distribution arrangement or other kinds of arrangements may be adopted. Each physiological signal sensing structure 102 may include a part of the flexible substrate 110, a piezoelectric sensing structure 120, and a damping structure 130.

The flexible substrate 110 may be attached or adhered to the user's body, so as to adapt to different body forms. This way, the one or more physiological signal sensing structures 102 of the flexible substrate 110 may be fittingly attached or adhered to the body, so as to obtain the signal. The flexible substrate 110 may have an additional layer of adhesive tape or a small sucker, so as to adhere to the body.

The shape of the piezoelectric sensing structure 120 may include one or more arc structures with curvatures. That is, the arc structures with curvatures protrude to the surface of the flexible substrate and may be disposed on the flexible substrate 110. In an embodiment, an adhering method may be adopted for attachment. The piezoelectric sensing structure 120 may include a protruding surface facing outwards, and a concave surface faces the flexible substrate 110. The piezoelectric sensing structure 120 may include a curved surface area and an edge area. The piezoelectric sensing structure 120 may include a first surface and a second surface. The second surface of the piezoelectric sensing structure 120 faces the flexible substrate. The curved surface area of the piezoelectric sensing structure 120 is an arc with a certain curvature, and the first surface thereof faces outward. The arc structure with a curvature of the piezoelectric sensing structure 120 includes a curved surface area 124 and an edge area 122. The curved surface area 124 may be located at a protruding area of the piezoelectric sensing structure 120 facing outwards, and the edge area 122 may be adhered on the flexible substrate 110. In an embodiment, the first surface and the second surface of the piezoelectric sensing structure 120 may include two conductive layers. A piezoelectric material layer is between the two conductive layers. For example, as shown, a piezoelectric material layer 128 is disposed between a top conductive layer 126 and a bottom conductive layer 127. A material of the piezoelectric material layer 128 may include organic material, inorganic material, or a composite of organic material and inorganic material. The organic material is, for example, Polyvinylidene Fluoride (PVDF) or Polyvinylidene Chloride (PVC), and the inorganic material is, for example silica (silicon dioxide), titania (Titanium dioxide), PZT (Lead zirconate titanate), PT (lead titanate), or BaTiO3. Since there may be a plurality of types of materials used in the piezoelectric material layer 128, all material that may be used in the piezoelectric material layer 128 is within the scope of the disclosure. The top conductive layer 126 and the bottom conductive layer 127 may be ultra-thin conductive films or conductive layers, and may be formed on the two side surfaces of the piezoelectric material layer 128 through several manners such as a deposition process, a printing process, or other processes. The material of the top conductive layer 126 and the bottom conductive layer 127 may be conductive material or metal material, such as nickel, silver, copper, or other alloys.

The damping structure 130 is disposed in a space between the flexible substrate 110 and the piezoelectric sensing structure 120. The material of the damping structure 130 may be material such as air, foam, or soft plastic, and is used to adjust the low frequency response of the piezoelectric sensing structure 120.

Next, the following will further describe the physiological signal sensing structure 102.

When the physiological signal sensing structure 102 is used, a plurality of the physiological signal sensing structures 102 may be attached or adhered to the chest of the user, so as to capture a plurality of physiological signals such as the sound of a heart beat (referred to as heart sound) from a plurality of different positions of the user's body. Since the acoustic impedance of the body may be $1.6 \times 10^6$ kg/m²s, the material selected as the piezoelectric sensing structure 120 has acoustic impedance around the same order as the body. Thus, the acoustic impedances may match to each other, and the energy of the amplitude of the heart sound may be transmitted to the piezoelectric sensing structure 120.

When the heart sound amplitude of the body reaches the surface of the skin, the heart sound amplitude drives the curved surface area 124 of the piezoelectric sensing structure 120 to generate piezoelectricity. Since the curved surface area 124 is located on the protruding surface of the piezoelectric sensing structure 120 facing outwards, the voltage generated at different curvatures of the piezoelectric sensing structure 120 with the arc structure receiving the same vertical stress will be different. That is, sensing the magnitude of the electromotive force is related to the curvature of the piezoelectric sensing structure 120. In the piezoelectric sensing structure 120 of the embodiment, through the design of the arc structure, the vertical pressure may be transferred to the horizontal piezoelectric sensing structure, causing a corresponding deformation. Because the piezoelectric sensing structure 120 has a horizontal sensitivity better than its vertical sensitivity, a low frequency vibration of the physiological signal may be more effectively captured. The following will present an embodiment for further description.

If the acoustic impedance of the muscles of a body exemplary to be $1.6 \times 10^6$ kg/m²s, and the acoustic impedance for air exemplary to be 344 kg/m²s, when the sound from within the body passes through muscles (impedance is assumed to be Z1), and passes through air (Z2), the reflectivity R when transmitting is $$R = \left(\frac{Z_1 - Z_2}{Z_1 + Z_2}\right)^2 = 99.88\%$$

Since it may be have difference between the impedances of the two transmission mediums, even differing by a few orders, thus, the signal may be weaken during the transmission process.

However, according to the embodiment of the disclosure, the material selected for the piezoelectric sensing structure may have acoustic impedance around the same or substantially the same order as the body. For example, when a material with an acoustic impedance of 2250 (m/s)×1740 (kg/m³)=$3.9 \times 10^6$(kg/m²s) is selected, the reflectivity during transmission is $$R = \left(\frac{Z_1 - Z_2}{Z_1 + Z_2}\right)^2 = 17.5\%$$

When sound from within the body passes through muscles, and then passes through the material of the piezoelectric sensing structure with acoustic impedance similar to the acoustic impedance of a body, the ratio of energy of reflected back to the body may be 17.5%, and the ratio of energy of entering the piezoelectric sensing structure may be 82.5%.

With this design, the impedances may match or substantially match and the energy of the amplitudes of the heart sound may be transmitted to the piezoelectric sensing structure.

The piezoelectricity generated by the piezoelectric sensing structure 120 may be the charges that accumulate in solid materials in response to applied mechanical stress. The piezoelectricity, or piezoelectric effect, is understood as the linear electromechanical interaction between the mechanical and the electrical state in crystalline materials with no inversion symmetry. The piezoelectric effect is a reversible process in that materials exhibiting the direct piezoelectric effect (the internal generation of electrical charge resulting from an applied mechanical force) also exhibit the reverse piezoelectric effect (the internal generation of a mechanical strain resulting from an applied electrical field). Piezoelectric materials also show the opposite effect, called converse piezoelectric effect, where the application of an electrical field creates mechanical deformation in the crystal. This converse piezoelectric effect is sometimes known as an electrostriction effect. Both of the piezoelectric effect and the converse piezoelectric effect are respectively regarded as a back and forth conversion between mechanical energy and electrical energy. This is extensively used today in multiple applications such as vibration detection and sound wave generation. When applied in vibration detection, a variety of piezoelectric sensors may be used, and when applied in signal generators, a variety of piezoelectric actuators can be used.

The piezoelectric material layer 128 of the embodiment may include PVDF material. Other piezoelectric materials can be used, such as polyvinyl chloride (PVC); P[VDF-TrFE], P[VDF-TFE] and P[VDF-HFP]; Composite of poly methyl methacrylate (PMMA) and PVDF; polyvinyl fluoride (PVF); and ferroelectric liquid crystals (FLCs) polymer. However, the embodiment is not limited thereto.

Figure 2:
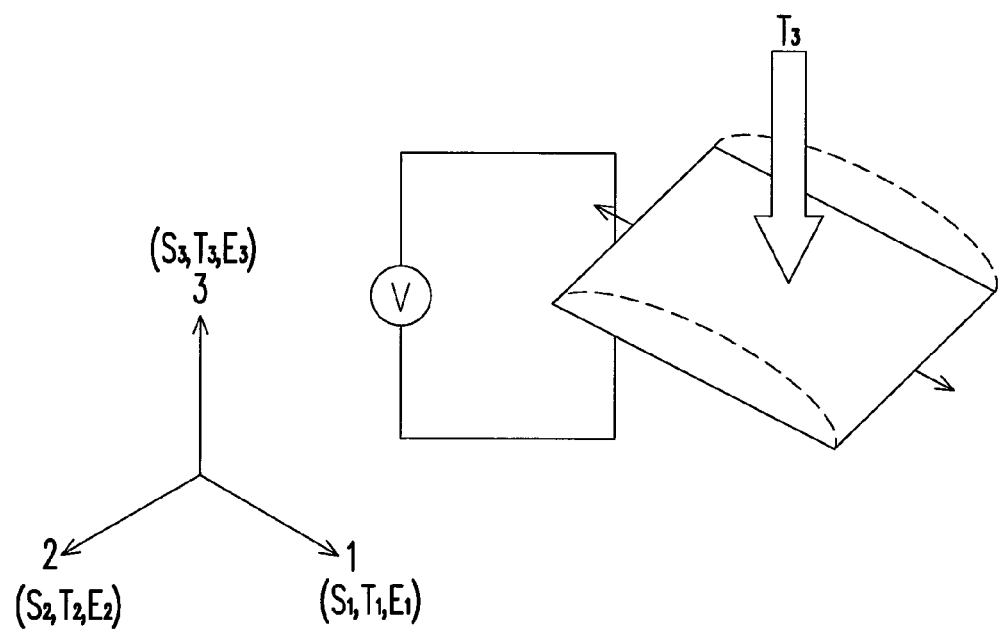
FIG. 2 is a schematic view illustrating a relationship between a direction of applying a force upon the arched piezoelectric sensing structure and the piezoelectricity reaction generated by the force.

The arc structure design of the piezoelectric sensing structure of an embodiment of the disclosure is further described. FIG. 2 is a schematic view illustrating a relationship between a direction of applying a force upon the arched piezoelectric sensing structure and the piezoelectric reaction generated by the force. As seen in the figure, the pressure is applied toward the top portion of the arc structure in the direction $T_3$, and deformation is in the $T_1$ direction. In the embodiment, a piezoelectric equation of the piezoelectric material of the piezoelectric sensing structure is shown below as piezoelectric equation (a)

$$S(T,E)=[s^E][T]+[d][E] \quad (a)$$

S is a strain matrix; T is a stress matrix (N/m$^2$) received by the material; E is an electric field matrix, herein representing the sensor electric field after receiving pressure; $s^E$ is a flexibility matrix, where the material is an isotropic material, and the matrix parameters are related to the mechanical material parameters of the material itself; [d] is a piezoelectric parameter matrix.

In the embodiment, since the direction $T_3$ applies pressure downwards towards the top portion of the arc structure, deformation may be created after pressure along the direction $T_1$.

According to the piezoelectric equation (a), the following equation (b.1) can be obtained:

$$\begin{bmatrix} S_1 \\ S_2 \\ S_3 \\ S_4 \\ S_5 \\ S_6 \end{bmatrix} = \begin{bmatrix} s_{11} & s_{12} & s_{13} & s_{14} & s_{15} & s_{16} \\ s_{21} & s_{22} & s_{23} & s_{24} & s_{25} & s_{26} \\ s_{31} & s_{32} & s_{33} & s_{34} & s_{35} & s_{36} \\ s_{41} & s_{42} & s_{43} & s_{44} & s_{45} & s_{46} \\ s_{51} & s_{52} & s_{53} & s_{54} & s_{55} & s_{56} \\ s_{61} & s_{62} & s_{63} & s_{64} & s_{65} & s_{66} \end{bmatrix} \begin{bmatrix} T_1 \\ T_2 \\ T_3 \\ T_4 \\ T_5 \\ T_6 \end{bmatrix} + \begin{bmatrix} d_{11} & d_{21} & d_{31} \\ d_{12} & d_{22} & d_{32} \\ d_{13} & d_{23} & d_{33} \\ d_{14} & d_{24} & d_{34} \\ d_{15} & d_{25} & d_{35} \\ d_{16} & d_{26} & d_{36} \end{bmatrix} \begin{bmatrix} E_1 \\ E_2 \\ E_3 \end{bmatrix} \quad (b.1)$$

The material used in the embodiment is PVDF piezoelectric material. This material is an isotropic material, and the matrix parameters are related to the mechanical material parameters of the material itself. Since the isotropic matrix is in the flexibility matrix, there is a matrix symmetrical feature, and so the matrix equation b.1 may be simplified to the equation b.2. Regarding the piezoelectric parameter matrix [d], since there may be five independent parameters in piezoelectric material, the PVDF can be thin, the piezoelectric parameters $d_{15}$ and $d_{24}$ are difficult to measure, can be assumed as zero.

$$\begin{bmatrix} S_1 \\ S_2 \\ S_3 \\ S_4 \\ S_5 \\ S_6 \end{bmatrix} = \begin{bmatrix} s_{11} & s_{12} & s_{12} & 0 & 0 & 0 \\ s_{12} & s_{11} & s_{12} & 0 & 0 & 0 \\ s_{12} & s_{12} & s_{11} & 0 & 0 & 0 \\ 0 & 0 & 0 & s_{44} & 0 & 0 \\ 0 & 0 & 0 & 0 & s_{44} & 0 \\ 0 & 0 & 0 & 0 & 0 & s_{44} \end{bmatrix} \begin{bmatrix} 0 \\ 0 \\ T_3 \\ 0 \\ 0 \\ 0 \end{bmatrix} + \begin{bmatrix} 0 & 0 & d_{31} \\ 0 & 0 & d_{32} \\ 0 & 0 & d_{33} \\ 0 & 0 & 0 \\ 0 & 0 & 0 \\ 0 & 0 & 0 \end{bmatrix} \begin{bmatrix} 0 \\ 0 \\ E_3 \end{bmatrix} \quad (b.2)$$

The parameters of the flexibility matrix are shown in b.3.

$$s_{11} = \frac{1}{Y}, \quad s_{12} = \frac{-v}{Y}, \quad s_{44} = \frac{2(1+v)}{Y} \quad (b.3)$$

When calculating b.3, Y is the Young's Modulus, and v is the Poisson's Ratio.

The strain is represented as:

$$S_1 = s_{12}T_3 + d_{31}E_3 \quad (c)$$

$$S_3 = s_{11}T_3 + d_{33}E_3 \quad (d)$$

$S_2 = S_4 = S_5 = S_6 = 0$

In the embodiment, the electric field is generated along the direction $T_3$, and is not generated along direction $T_1$ and $T_2$, as shown in equation b.2. As seen in equation (c) and (d), strain and the sensor electric field are proportional to each other. Also, the piezoelectric strain parameter $d_{31}$ is better than $d_{33}$, and thus when pressure is received in the direction $T_3$, as seen in FIG. 2, the arc structure will deform along the direction $T_1$, generating a bigger strain. The deformation along the direction $T_3$ is smaller, and the strain is smaller. Thus, along direction $T_1$, a greater sensor electric field is generated. Therefore, when the arc structure of the piezoelectric sensing structure receives pressure in the direction $T_3$, it will deform along direction $T_1$, so as to obtain greater signal output and sensing capability.

Figure 3A:
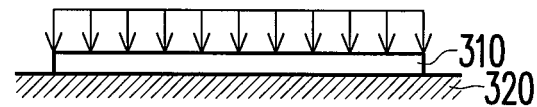
FIGS. 3A to 3C are schematic views of piezoelectric sensing structures with different arcs according to some embodiments of the disclosure.
Figure 3B:
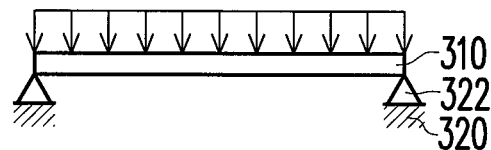
Figure 3C:
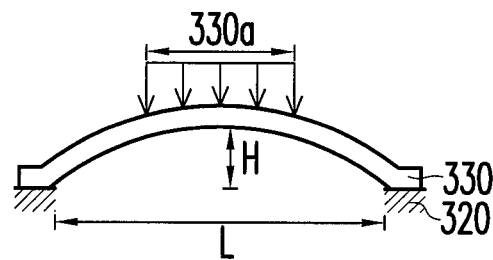

In further detail, FIGS. 3A to 3C are schematic views of piezoelectric sensing structures with different arcs illustrating different embodiments of the disclosure. FIG. 3A is a schematic diagram showing a piezoelectric sensing structure 310 planarly attached or adhered on a carrier 320, being applied a vertical pressure. FIG. 3B is a schematic diagram showing a piezoelectric sensing structure 310 being applied a vertical pressure supported by two supporting structures fixed to a carrier 320. FIG. 3C shows a piezoelectric sensing structure 330 with a curvature having a protruding surface facing outwards, and an edge area planarly attached or adhered to a carrier 320. A curved surface area 330a is outwardly curved, and an external force is applied to the position of the curved surface area 330a. In an embodiment of the disclosure, as seen in FIG. 3A to FIG. 3C, the piezoelectric sensing structure receives the same vertical stress at different curvatures, generating different electromotive force. The finite element method may be used to construct the numerical analysis calculation model of the embodiment. Through the comparison results obtained by analysis calculation, an arc structure design increases the sensitivity of heart sound auscultation sensing components and obtains a larger sensed electromotive force when compared to the flat surface structure designs.

The vertical stress applied in the embodiment may be 70 grams (1 Psi of pressure, or lb/in$^2$). The area of the piezoelectric sensing structure may be 1 cm$^2$, and the thickness may be 0.04 mm.

Figure 3D:
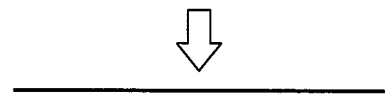
FIGS. 3D to 3E are schematic views of non-arc-shaped piezoelectric sensing structure, and the voltage generated by applying the vertical stress on the piezoelectric sensing structure according to an embodiment of the disclosure.

As seen in FIG. 3D, if the piezoelectric sensing structure is placed in a non-arc-shaped plane, when receiving vertical stress, calculations from numerical analysis show that the electromotive force obtained is around 4.67E-12 volts.

Figure 3E:
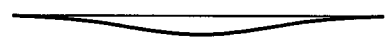

If the piezoelectric sensing structure is placed on two protruding support structures (herein the two protruding support structures are the same height, as seen in FIG. 3B), when receiving vertical stress, calculations from numerical analysis show that the electromotive force obtained is around −1.70E-10 volts, shown in FIG. 3E.

Figure 3F:
FIG. 3F is a schematic view of a piezoelectric sensing structure with a certain curvature receiving a vertical stress, and the electromotive force generated by applying the vertical stress on the piezoelectric sensing structure, according to an embodiment of the disclosure.

Furthermore, as seen in FIG. 3C, if the two ends of the piezoelectric sensing structure 120 are fixed, and the middle area is an arc structure, when receiving vertical stress, calculations from numerical analysis show that the electromotive force obtained is around 2.26E-07 volts, shown in FIG. 3F. From the above data, it can be seen that the electromotive force generated by the piezoelectric sensing structure of FIG. 3F is five orders (10$^5$, over 1000 times more) higher than the electromotive force generated by the piezoelectric sensing structure of FIG. 3D.

Figure 3G:
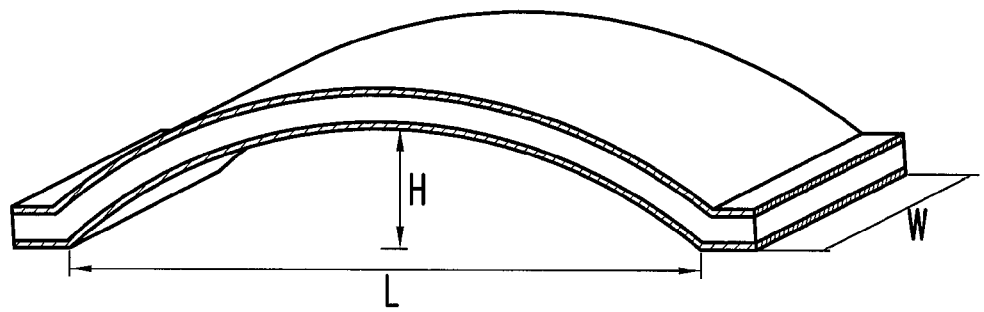
FIG. 3G is a schematic side view of a piezoelectric sensing structure of the disclosure with a certain curvature according to an embodiment of the disclosure.

Referring to FIG. 3G, the piezoelectric sensing structure 120 with an arc structure has a top and bottom surface each having a conductive layer. The change of the arc curvature radius ($\kappa$), is shown in the following equation:

$$\kappa = [(L/2)^2 + (H)^2]/2H \quad \text{Curvature radius formula:}$$

L is the length of the arc structure of the piezoelectric sensing structure. H is the height of the arc structure of the piezoelectric sensing structure. W is the width of the arc structure of the piezoelectric sensing structure. As seen in the above formula, the curvature radius is related to the arc length (L) and height (H). Therefore, through the change in length and height of the arc structure, the curvature radius of the arc structure is changed. Thus, as shown through analysis and calculation, the change in height and length of the arc structure causes a change in the curvature radius. When the top end of the arc structure receives similar pressure, at different parameters the sensed voltage generated is changed. The trends are shown in Table 1. As described in the above design, the change in length and height of the arc structure can be explored, so that the change in curvature radius has a relationship with the generated sensed voltage. As seen in Table 1, a design parameter range can be found.

TABLE 1

Table 1: Arc structure curvature radius and sensing voltage

| W(mm) | L(mm) | H(mm) | κ(mm) | Voltage(V) |
|---|---|---|---|---|
| 10 | 20 | 2.0 | 26.0 | 7.19E−08 |
|  |  | 1.5 | 34.1 | 1.00E−07 |
|  |  | 1.0 | 50.5 | 1.41E−07 |
|  |  | 0.5 | 100.0 | 2.26E−07 |
|  | 15 | 2.0 | 15.1 | 2.62E−08 |
|  |  | 1.5 | 19.5 | 4.65E−08 |
|  |  | 1.0 | 28.6 | 7.42E−08 |
|  |  | 0.5 | 56.5 | 1.26E−07 |
|  | 10 | 2.0 | 7.25 | 4.04E−10 |
|  |  | 1.5 | 9.08 | 1.06E−08 |
|  |  | 1.0 | 13.0 | 2.62E−08 |
|  |  | 0.5 | 25.3 | 5.31E−08 |
|  | 5 | 2.0 | 2.56 | 8.40E−11 |
|  |  | 1.5 | 2.83 | 1.25E−10 |
|  |  | 1.0 | 3.63 | 6.83E−10 |
|  |  | 0.5 | 6.50 | 9.63E−09 |

Thus, in the piezoelectric sensing structure of the embodiment of the disclosure, through the design of the arc structure, a vertical pressure may be transferred to deform the horizontal piezoelectric sensing structure. The piezoelectric sensing structure having a horizontal sensitivity better than its vertical sensitivity and thus being able to amplify piezoelectric sensing, a low frequency vibration of a physiological signal may be more effectively captured.

Figure 4:
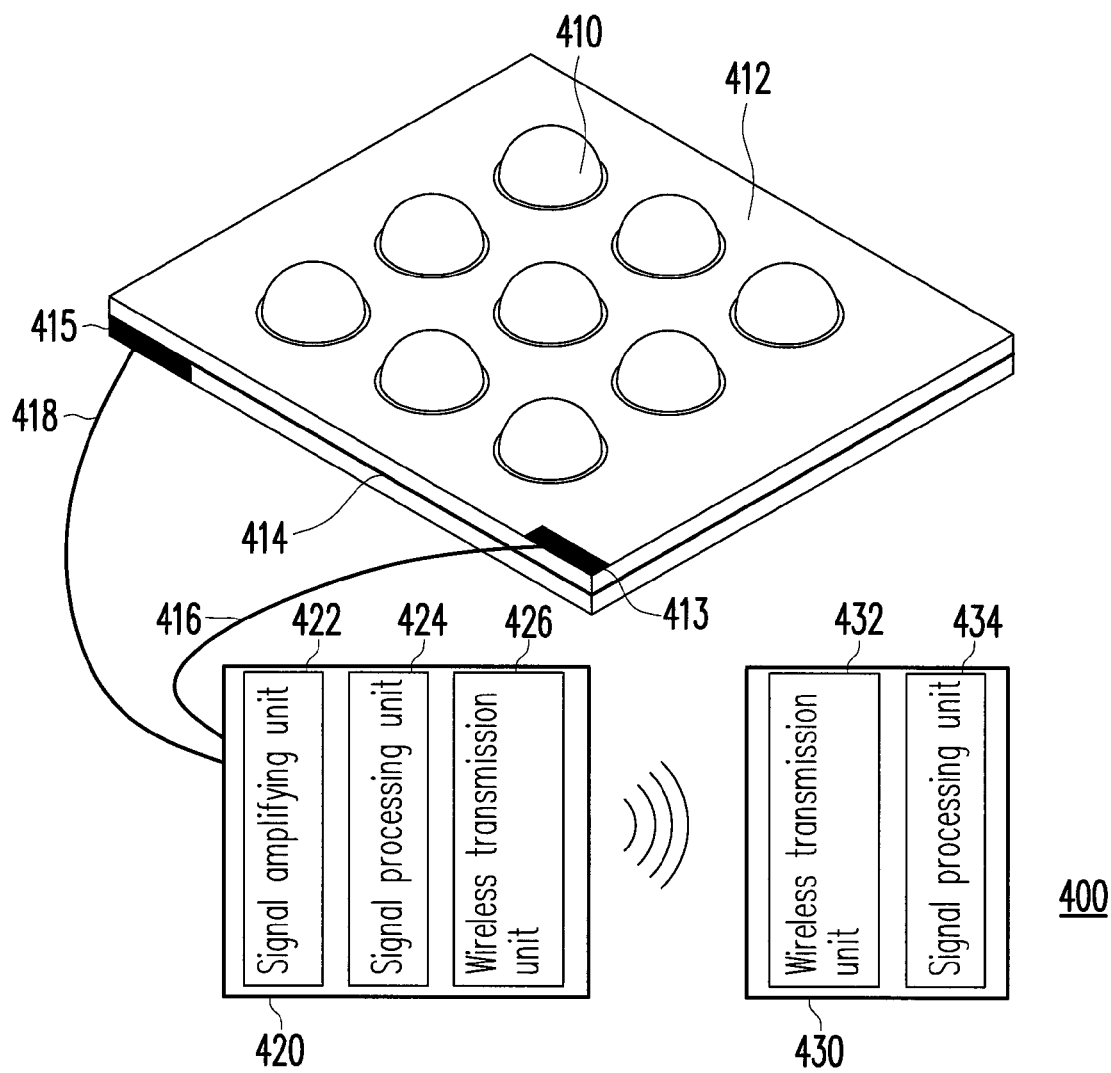
FIG. 4 is a schematic view of a physiological signal sensor structure according to another embodiment of the disclosure.

In another embodiment, FIG. 4 is a schematic side view of a physiological signal sensor structure according to another embodiment of the disclosure.

A flexible stethoscope 400 may include a plurality of physiological signal sensing structures 410, arranged on a flat surface, such as the same flexible substrate. In an embodiment, an array-type distribution arrangement may be adopted. The physiological signal sensing structures 410 may form the flexible stethoscope 400 through a pattern with a plurality of arrays, so as to broaden the sensing area of the physiological signal. The number of the arrays of the physiological signal sensing structures 410 is determined according to design, and variation of the number of the arrays does not depart from the scope of the embodiment.

Referring to FIG. 4, when physiological signals are obtained through multiple physiological signal sensing structures 410, the signals are transmitted to a signal processing device at a back end for further processing and analysis of the physiological signals. In the embodiment, the two conductive layers of the piezoelectric sensing structure of each physiological signal sensing structure 410, for example the top conductive layer 126 and the bottom conductive layer 127 on the two sides of the piezoelectric sensing structure 120 of FIG. 1, are respectively electrically connected to two conductive layers 412 and 414 of the flexible stethoscope 400 through the electrically connecting pads 413 and 415. The conductive layers 412 and 414 are respectively connected to a signal processing apparatus 420 at a previous stage through electrically connecting circuits 416 and 418. The signals sensed by the physiological signal sensing structure 410 are transmitted to the signal processing apparatus 420 through the electrically connecting circuits 416 and 418, and the signal processing apparatus 420 transmits the obtained physiological signal to the signal processing apparatus 430 at the back end through a wireless method.

In an embodiment, the signal processing apparatus 420 at the previous stage may include a signal amplifying unit 422, a signal processing unit 424, and a wireless transmission unit 426. A signal amplifying unit 422 is used to amplify the physiological signals sensed by the physiological signal sensing structures 410, thus aiding the signal processing at the back end. The signal processing unit 424 is used to process the amplified physiological signals, thus aiding the transmission process. The wireless transmission unit 426 then transmits data to the signal processing apparatus 430 at back end. In an embodiment, the back end signal processing apparatus 430 can include a wireless transmission unit 432 and a signal processing unit 434. The wireless transmission unit 432 receives the amplified and processed physiological signals, and transmits the signals to the signal processing unit 434 to read and display the physiological conditions. The embodiment can also use wired transmission to transmit signals.

Figure 5A:
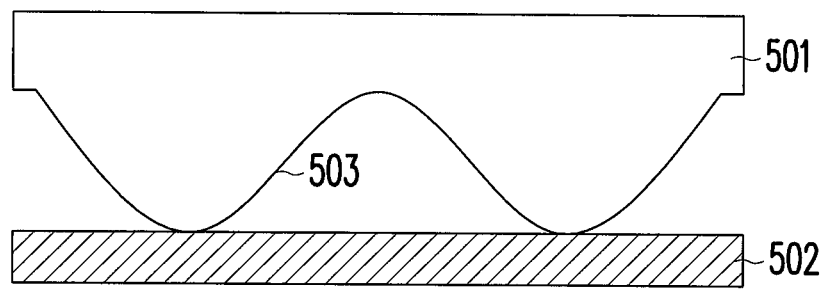
FIG. 5A is a schematic view of a method of manufacturing a piezoelectric sensing structure having an arc structure according to an embodiment of the disclosure.
Figure 5B:
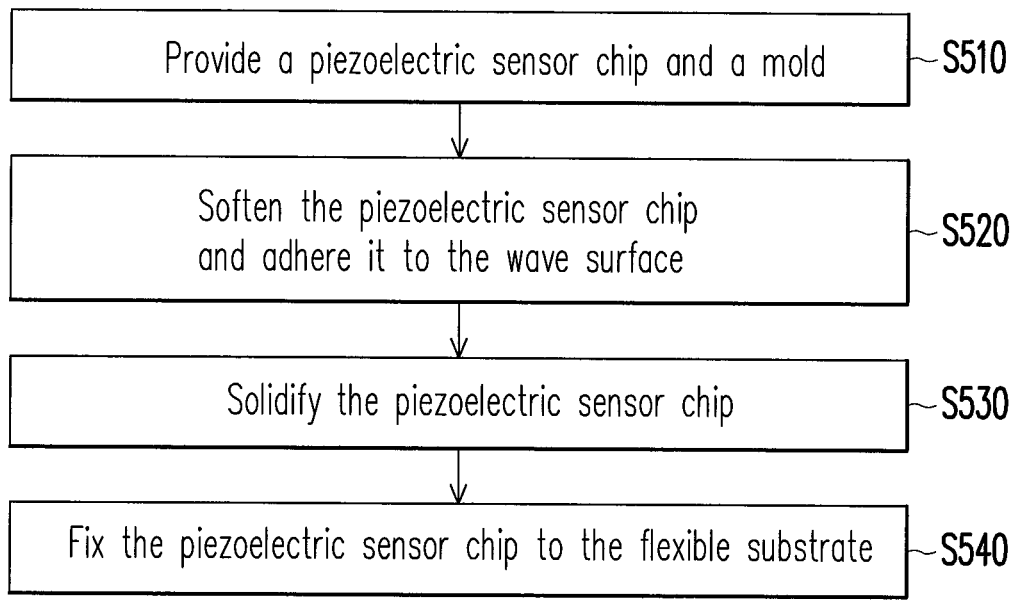
FIG. 5B is a flow chart of a method of manufacturing a physiological signal sensor structure according to an embodiment of the disclosure.

Please refer to FIGS. 5A and 5B. The disclosure provides an embodiment of a method of manufacturing a physiological signal sensing structure. FIG. 5A is a schematic view of a method of manufacturing a piezoelectric sensing structure having an arc structure according to an embodiment of the disclosure. FIG. 5B is a flow chart of a method of manufacturing a physiological signal sensor structure according to an embodiment of the disclosure.

In an embodiment, the method of manufacturing the physiological signal sensing structure includes the following steps. A piezoelectric sensor sheet 502 and a mold 501 are provided. The mold 501 has a surface including a non-continuous wave surface 503 (step S510). The curvature of the wave surface 503 is determined according to design, so that the physiological signal sensing structure may be sensitive enough to capture physiological signals. The piezoelectric sensor sheet 502 is softened through, for example, a heating process. Through a pressurizing processing, the piezoelectric sensor sheet chip 502 is adhered onto the wave surface 503 (step S520). The piezoelectric sensor sheet 502 is solidified (step S530) through, for example, cooling. That is, in this step, the piezoelectric sensor sheet 502 may form into a piezoelectric sensing structure with an arc structure. the piezoelectric sensor sheet 502 may be fixed to the flexible substrate (step S540).

In an embodiment, step S520 may include drawing out the air between the piezoelectric sensor sheet 502 and the wave surface 503. By the manner, a vacuum condition can suck the piezoelectric sensor sheet 502 to the wave surface 503, so that the piezoelectric sensor sheet 502 forms into a piezoelectric sensing structure with multiple arc structures. In another embodiment, the step S520 includes pressing the piezoelectric sensor sheet 502 onto the wave surface 503. That is, a mold pressing method is used so that the piezoelectric sensor sheet 502 forms into a piezoelectric sensing structure with multiple arc structures.

Figure 5C:
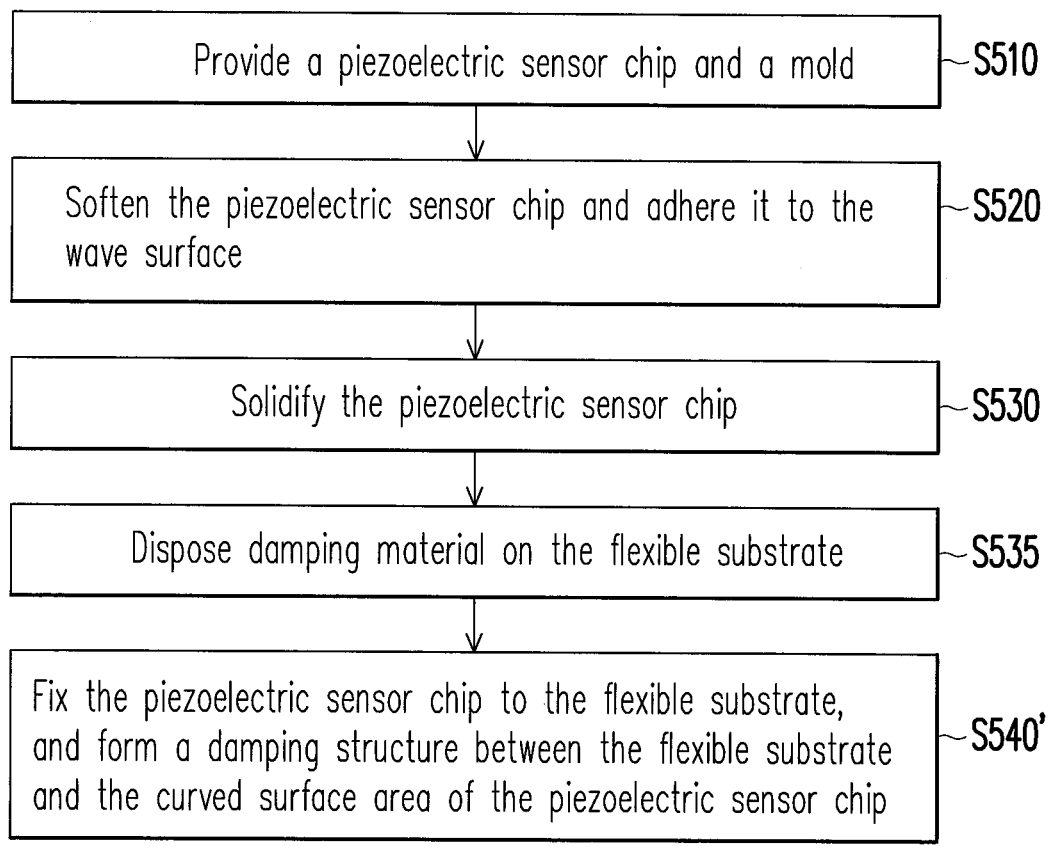
FIG. 5C is a flow chart of a method of manufacturing a physiological signal sensor structure according to another embodiment of the disclosure.

In further detail, for example, in order to improve the low frequency response of the physiological sensor, foam or soft plastic may be additionally filled between the piezoelectric sensor sheet and the flexible substrate. Referring to FIG. 5C, FIG. 5C is a flow chart of a method of manufacturing a physiological signal sensor structure according to another embodiment of the disclosure. The difference between FIG. 5C and FIG. 5B is the step S535 and the step S540'. The steps S510, S520, and S530 are the same, and are not repeated herein. In step S530, the piezoelectric sensor sheet is solidified to become a piezoelectric sensor sheet with multiple arc structures. In step S535, damping material is disposed over the flexible substrate 110. In step S540', the piezoelectric sensor sheet is fixed to the flexible substrate, and a damping structure is formed between the flexible substrate and the curved surface area of the piezoelectric sensor sheet. The damping material can be material such as air, foam, or soft plastic, and is used to adjust the low frequency response of the piezoelectric sensing structure.

In an embodiment of the disclosure, the physiological signal sensing structure or the flexible stethoscope structure may include an amplifying structure. When the sound of the physiological signals of the body, for example heart sound or lung sound, reaches the surface of the skin, the amplitude of the sound drives the amplifying structure. Then the amplifying structure uses, for example, a protruding structure to transmit the sound to the piezoelectric sensing structure, so as to amplify the amplitude of the sound that is transmitted, and conveniently sense and obtain the physiological signal of the body.

Figure 6:
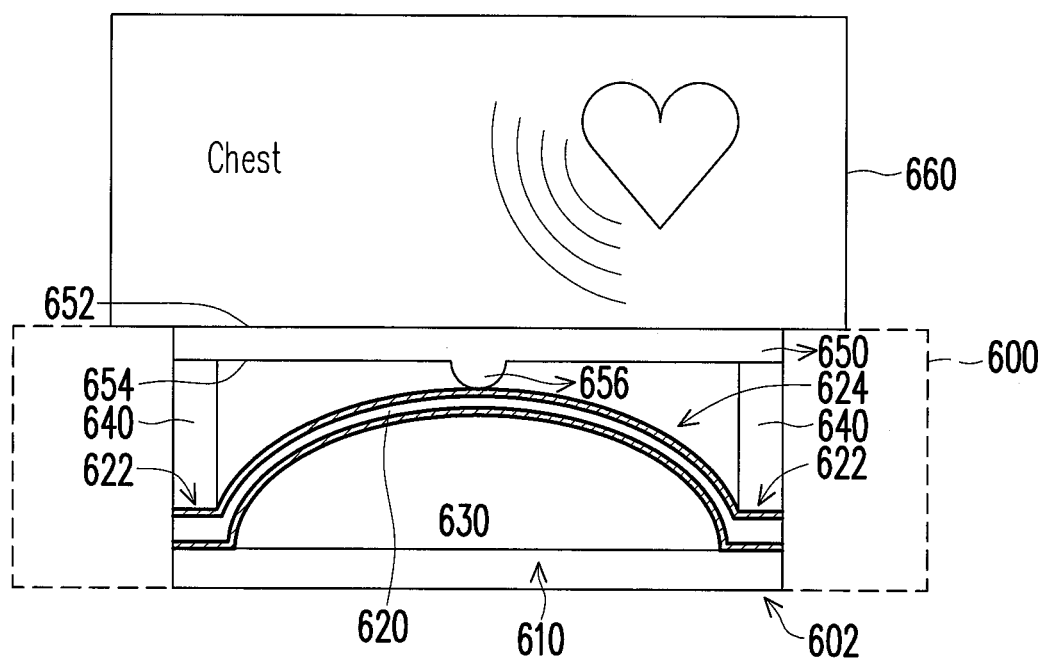
FIG. 6 is a schematic view of a physiological signal sensor structure according to an embodiment of the disclosure.

In an embodiment, please refer to FIG. 6 for a more further illustration. FIG. 6 is a schematic view of a physiological signal sensor structure according to an embodiment of the disclosure. A flexible stethoscope 600 includes one or more physiological signal sensing structures 602. Herein a single physiological signal sensing structure 602 is described, and the number physiological signal sensing structures 602 are arranged as an array, to simultaneously sense physiological signals. The physiological signal sensing structure 602 includes a flexible substrate 610, a piezoelectric sensing structure 620, a damping structure 630, a support body 640, and an amplifying structure.

In the embodiment, the flexible stethoscope 600 has further included an amplifying structure of the physiological signal sensing structure. In an embodiment, the amplifying structure may include a support body 640 and an amplifier structure 650. The support body 640 is disposed on the edge area 622 of the piezoelectric sensing structure 620. An edge of the amplifier structure 650 is disposed on the support body 640. The amplifier structure 650 includes a body. The body includes a first surface 652 and a second surface 654. The body includes a protruding portion 656 that is a protruding structure at the middle area of the second surface 654. The protruding portion 656 can be contacted to the piezoelectric sensing structure 620. In another embodiment, the protruding portion 656 is not contacted to the piezoelectric sensing structure 620. However, the distance may be set so that the amplitude of when the amplifying structure vibrates, a top portion of the protruding portion 656 contacts the piezoelectric sensing structure 620.

When being used, the first surface 652 of the amplifier structure 650 is planarly attached or adhered to the surface of the skin of the user. The protruding portion 656 of the second surface 654 is close to or directly contacts the top portion of the curved surface area 614 of the piezoelectric sensing structure 620 with a curvature. The contact method may be a point contact method or a small area attachment or adherence contact. When the sound of the physiological signal of the body, for example heart sound or lung sound, reaches the skin surface, the amplitude of the sound drives the amplifier structure 650. The amplifier structure 650 then transmits the sound to the piezoelectric sensing structure 620 by using the protruding portion 656. The transmitted amplitude of the sound can be amplified, so as to conveniently sense and obtain the physiological signal of the body.

The protruding portion 656 may be made through, for example, a bump screen printing method, but is not limited thereto. The material of the amplifier structure 650 can be any material that has an acoustic impedance in the same or close to the same order as the acoustic impedance of muscles, such as plastic. This consideration is so that when sound is transmitted, there is a good impedance matching. This way, most of the physiological signals (such as heart sound) may be transmitted to the flexible stethoscope 600.

The physiological signal sensing structure or the stethoscope provided by the disclosure avoids a sound collector cavity design. This way, the thickness of the stethoscope may be reduced to the order of millimeters, and is useful for portable designs. Heart sound signals directly press the piezoelectric material with a certain curvature, to achieve low frequency (1 Hz) detection. Omitting a second mechanical signal amplification by the cavity structure may reduce distortion rate.

The thin and flexible physiological signal sensing structure or the flexible stethoscope provided by the disclosure can have a flexible and large area array design that is suitable for mass production.

In order for heart sound to be detected as a physiological signal, it can be in the range of 0.1 Hz to 1 kHz, and is further limited by the physical restrictions of wavelength. Thus, conventional sound collectors will be designed with a specific volume (in the order of centimeters). Therefore, when designing the sensor of the disclosure, the structure may be flexible so as to be comfortably contacted with skin, and the thickness of the structure is in the order of millimeters. The physiological signal sensing structure or the flexible stethoscope provided by the disclosure can detect low frequency heart sound, improves measuring precision, and is flexible.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A physiological signal sensing structure, comprising:
a flexible substrate;
a piezoelectric sensing structure, disposed over the flexible substrate, wherein the piezoelectric sensing structure at least comprises a curved surface area and an edge area, the piezoelectric sensing structure comprises a first surface and a second surface, the second surface faces the flexible substrate, and the piezoelectric sensing structure has an arc with a curvature, and the first surface of the piezoelectric sensing structure faces outward; and
a damping structure, disposed between the flexible substrate and the piezoelectric sensing structure.

2. The structure as claimed in claim 1, wherein the piezoelectric sensing structure comprises a top conductive layer, a bottom conductive layer, and a piezoelectric material layer located between the top conductive layer and the bottom conductive layer.

3. The structure as claimed in claim 2, wherein the piezoelectric material layer comprises a PVDF or a material combination of Polyvinylidene Fluoride (PVDF).

4. The structure as claimed in claim 2, wherein the piezoelectric material layer comprises an electroactive polymer (EAP).

5. The structure as claimed in claim 1, wherein a material of the damping structure is an air, a foam, or a soft plastic.

6. The structure as claimed in claim 1, further comprising an amplifying structure, disposed over the curved surface area of the first surface of the piezoelectric sensing structure, wherein a side of the amplifying structure contacts the piezoelectric sensing structure or maintains a distance from the piezoelectric sensing structure.

7. The structure as claimed in claim 6, wherein the amplifying structure comprises a support body and an amplifier structure, the support body is disposed on the edge area of the first surface of the piezoelectric sensing structure, and an edge of the amplifier structure is disposed on the support body, wherein a middle area of a side surface of the amplifier structure contacting the support body contacts the piezoelectric sensing structure or maintains the specific distance from the piezoelectric sensing structure.

8. The structure as claimed in claim 7, wherein the amplifier structure comprises a body and a protruding portion, the body comprises a first surface and a second surface, the first surface is a plane surface, and the protruding portion is located at a middle area of the second surface, wherein the protruding portion contacts the piezoelectric sensing structure or maintains the distance from the piezoelectric sensing structure.

9. The structure as claimed in claim 8, wherein the material of the body comprises a plastic.

10. A stethoscope, comprising:
a plurality of physiological signal sensing structures, wherein each of the plurality of physiological signal sensing structures comprises:
a flexible substrate;
a piezoelectric sensing structure, disposed over the flexible substrate, wherein the piezoelectric sensing structure comprises a curved surface area and an edge area, the piezoelectric sensing structure comprises a first surface and a second surface, the second surface faces the flexible substrate, and the piezoelectric sensing structure has an arc with a curvature, and the first surface of the piezoelectric sensing structure faces outward; and
a damping structure, disposed between the flexible substrate and the piezoelectric sensing structure.

11. The stethoscope as claimed in claim 10, wherein each of the plurality of physiological signal sensing structures comprises a top conductive layer, a bottom conductive layer, and a piezoelectric material layer located between the top conductive layer and the bottom conductive layer.

12. The stethoscope as claimed in claim 11, further comprising a first signal processing apparatus, configured to connect to the top conductive layers and the bottom conductive layers of the plurality of physiological signal sensing structures, for obtaining a sensed physiological signal, and generating a corresponding signal through amplification processing upon the sensed physiological signal, thereby the physiological signal is received an external second signal processing apparatus by transmitting the corresponding signal.

13. The stethoscope as claimed in claim 12, wherein the first signal processing apparatus comprises a wireless transmission unit, wherein the corresponding signal is wirelessly transmitted by the wireless transmission unit to the second signal processing apparatus.

14. The stethoscope as claimed in claim 10, wherein the piezoelectric sensing structure comprises a top conductive layer, a bottom conductive layer, and a piezoelectric material layer located between the top conductive layer and the bottom conductive layer.

15. The stethoscope as claimed in claim 14, wherein the piezoelectric material layer comprises a PVDF or a material combination of Polyvinylidene Fluoride (PVDF).

16. The stethoscope as claimed in claim 14, wherein the piezoelectric material layer comprises an electroactive polymer (EAP).

17. The stethoscope as claimed in claim 10, wherein a material of the damping structure is an air, a foam, or a soft plastic.

18. The stethoscope as claimed in claim 10, further comprising an amplifying structure, disposed over the curved surface area of the first surface of the piezoelectric sensing structure, wherein a side of the amplifying structure contacts the piezoelectric sensing structure or maintains a distance from the piezoelectric sensing structure.

19. The stethoscope as claimed in claim 18, wherein the amplifying structure comprises a support body and an amplifier structure, the support body is disposed on the edge area of the first surface of the piezoelectric sensing structure, and an edge of the amplifier structure is disposed on the support body, wherein a middle area of a side surface of the amplifier structure contacting the support body contacts the piezoelectric sensing structure or maintains the distance from the piezoelectric sensing structure.

20. The stethoscope as claimed in claim 19, wherein the amplifier structure comprises a body and a protruding portion, the body comprises a first surface and a second surface, the first surface is a plane surface, and the protruding portion is located at a middle area of the second surface, wherein the protruding portion contacts the piezoelectric sensing structure or maintains the distance from the piezoelectric sensing structure.

21. The stethoscope as claimed in claim 18, wherein the material of the body comprises a plastic.

\* \* \* \* \*